US 8,093,429 B2

(12) United States Patent
Hidaka et al.

(10) Patent No.: US 8,093,429 B2
(45) Date of Patent: Jan. 10, 2012

(54) FLUOROAMINE HAVING PERFLUOROALKYL GROUP, PROCESS FOR PRODUCING THE SAME, METHOD OF FLUORINATION THEREWITH, AND METHOD OF RECOVERING AMIDE HAVING PERFLUOROALKYL GROUP

(75) Inventors: Toshio Hidaka, Ibaraki (JP); Takafumi Yoshimura, Niigata (JP); Shoji Hara, Hokkaido (JP); Tsuyoshi Fukuhara, Hokkaido (JP)

(73) Assignees: National University Corporation Hokkaido University, Hokkaido (JP); Mitsubishi Gas Chemical Company, Inc., Tokyo (JP)

( * ) Notice: Subject to any disclaimer, the term of this patent is extended or adjusted under 35 U.S.C. 154(b) by 489 days.

(21) Appl. No.: 12/302,362

(22) PCT Filed: May 31, 2007

(86) PCT No.: PCT/JP2007/061075
§ 371 (c)(1),
(2), (4) Date: Nov. 25, 2008

(87) PCT Pub. No.: WO2007/139182
PCT Pub. Date: Dec. 6, 2007

(65) Prior Publication Data
US 2009/0198086 A1    Aug. 6, 2009

(30) Foreign Application Priority Data
May 31, 2006  (JP) .................... 2006-152140

(51) Int. Cl.
*C07C 211/27*  (2006.01)
(52) U.S. Cl. ......... 564/366; 564/336; 564/373; 564/510
(58) Field of Classification Search .............. 564/336, 564/373, 510, 366
See application file for complete search history.

(56) References Cited

U.S. PATENT DOCUMENTS

| 3,933,831 | A |   | 1/1976 | De Pasquale et al. |
| 5,859,247 | A | * | 1/1999 | Curran et al. ............ 546/2 |
| 6,803,475 | B2 |   | 10/2004 | Wipf et al. ............ 556/465 |
| 2005/0085474 | A1 | * | 4/2005 | Ebenbeck et al. ......... 514/237.5 |

FOREIGN PATENT DOCUMENTS

| EP | 0 456 093 A2 | 11/1991 |
| EP | 1 422 216 A1 | 5/2004 |
| JP | 08-291084 | 11/1996 |
| JP | 2000-154155 | 6/2000 |
| JP | 2002-293828 | 10/2002 |
| JP | 2004-123605 | 4/2004 |
| WO | WO 03/020685 A1 | 3/2003 |

OTHER PUBLICATIONS

M. Misono, "Green Chemistry: Concept and Practice", *Journal of Organic Synthetic Chemical Society of Japan*, vol. 61, No. 5, pp. 406-412 (2003).
R. Ilhyong, et al., *Chemistry*, vol. 57, No. 5, pp. 20-23 (2002).
Supplementary European Search Report and European Search Opinion dated Sep. 16, 2009, for Application No. EP 07 76 6998.
R. J. DePasquale, "An Approach to the Synthesis of F-Tertiary Amines", *Journal of Organic Chemistry* vol. 43, No. 9, 1978, pp. 1727-1729. (XP-002541140).
M. Kuroboshi, et al., "A Convenient Synthesis of Perfluoroalkylated Amines by Oxidative Desulfurization-Fluorination", *Tetrahedron Letters* vol. 35, No. 23, 1994. pp. 3983 and 3984. XP-002541141).
L. E. Kiss, et al., "Methyl Perfluorooctanethionate as a Tool for Indirect Perfluoroalkylmethylation and Perfluoroalkylation of Amines", *SYNLETT*, Nov. 1998, pp. 1243-1245. (XP-002541142).
Wojcieoh Dmowski et al., Dialkyl-x, x-Difluoro Benzylamines and Dialkyl (trifluromoethyl)-Amines-Novel Florinating Reagents, Journal of Fluorine Chemistry, 1983, vol. 23, pp. 2-19-228.
Seiji Takeuchi et al., Fusai Shokubai No Nyu Gurin Fasshon : Fluorous Ponytail, Chemistry, 2002, vol. 57, pp. 16-20.
C.C. Tzchuke et al., Modern Separation Techniques for the Efficient Workup in Organic Synthesis, Angewamdte Chemie International Edition, 2002, vol. 41, pp. 3964-400.

* cited by examiner

*Primary Examiner* — Shailendra Kumar
(74) *Attorney, Agent, or Firm* — Antonelli, Terry, Stout & Kraus, LLP.

(57) ABSTRACT

Provided are a fluorous-tag-introduced fluoroamine of a general formula (I), its production method, a method of fluorination of a substrate having functional group containing oxygen with the fluoroamine serving as a fluorinating agent, and a method of recovering a fluorous-tag-introduced amide after the fluorination. The fluoroamine and its production method, as well as the fluorination method with the fluoroamine and the method of recovery of a fluorous-tag-introduced amide are ecological and advantageous in industrial use, as the load for separating and collecting the product after the fluorination with the fluoroamine serving as a fluorinating agent is small.

$$R_0-\underset{F}{\underset{|}{C}}\underset{F}{\overset{|}{-}}N\underset{R_2}{\overset{R_1}{<}} \quad (I)$$

(In the formula, $R_0$ is an alkyl group or an aryl group having substituent(s) of $Rf-(CH_2)_m-$; Rf is a perfluoroalkyl group; m is from 0 to 2; $R_1$ and $R_2$ each are an alkyl group or an aryl group.)

6 Claims, No Drawings

FLUOROAMINE HAVING PERFLUOROALKYL GROUP, PROCESS FOR PRODUCING THE SAME, METHOD OF FLUORINATION THEREWITH, AND METHOD OF RECOVERING AMIDE HAVING PERFLUOROALKYL GROUP

This application is a 371 of PCT/JP2007/061075, filed May 31, 2007.

TECHNICAL FIELD

The present invention relates to a perfluoroalkyl group-having fluoroamine and its production method, to a novel method of fluorination of a substrate having functional group containing oxygen with the fluoroamine, and to a method of recovering a perfluoroalkyl group-having amide.

BACKGROUND ART

Many methods have been known for a long time for halogenation of organic compounds. As a halogenating agent in these, halogen simple substances, hydrogen halides, or halogen-containing phosphorus or sulfur compounds are well used. However, these halogenating agents are problematic in point of their safety as they are toxic. In particular, since the environmental load in treating their wastes is large these days, use of these halogenating agents on an industrial scale may be difficult in future.

Various halogen-containing compounds are known, which have characteristic properties derived from the halogen atom therein. Above all, many fluorine-containing compounds have specific physiological activities and functions, and their applications in various fields are under investigation. In particular, the importance of fluorine-containing compounds in the filed of medicines, agricultural chemicals and the like is increasing more and more.

Few fluorine-containing compounds exist in nature, and it is necessary to introduce fluorine atom to the compound by organosynthetic method. Accordingly, industrially-useful fluorinating agents and fluorination methods with a low environmental load are strongly desired, and their studies and developments are being made in many aspects.

Recently, novel fluoroamine compounds have been developed, which can selectively fluorinate a functional group with oxygen, sulfur, halogen or the like and which are thermally stable, low-toxic and easily handlable have been developed (e.g., see Patent Reference 1). One typical compound of the type is N,N-diethyl-α,α-difluoro-(3-methylbenzyl)amine. This compound changes back, after used for fluorination of a substrate, to N,N-diethyl-meta-toluamide, which is a starting compound for this compound; and its excellent advantageous is that the toluamide can be recovered and reused.

However, N,N-diethyl-meta-toluamide has a high boiling point and is a good solvent by itself, and therefore it is hard to say that the recovery of the compound is easy, as the compound is well soluble with various organic compounds. As a result, the energy consumption in the entire process increases, and the wastes increase; and therefore the method is not satisfactory in point of the environmental load.

Recently, studies of green chemistry for the purpose of reducing the environmental load have become active, and development of ecological processes is one important theme in the art. For example, a polymer-supported halogenating agent and the like has been developed in consideration of recovery and recycle of starting material (e.g., see Patent References 2 and 3).

On the other hand, a field of fluorous chemistry of which the studies have just begun in these ten several years is specifically noted from the viewpoint of green chemistry. Fluorous chemistry is an art using the property of highly-fluorinated fluoro compounds that are hardly soluble in ordinary organic solvents and water but are readily soluble in fluorous solvents (fluorous property) (e.g., see Non-Patent References 1 and 2). The fluorous property may be given to compounds by introducing a fluorous-tag (perfluoro group) into them; however, a fluorinating agent with such a fluorous-tag introduced thereinto and its production method, and an ecological fluorination method using it are unknown.

Patent Reference 1: WO03/020685
Patent Reference 2: JP-A 2000-154155
Patent Reference 3: JP-A 2002-293828
Non-Patent Reference 1: Makoto Misonoo, the Journal of Organic Synthetic Chemical Society of Japan, 61, 406 (2003)
Non-Patent Reference 2: Ryu Ilhyong, Hiroshi Matubara, Chemistry, 57, 20 (2002)

DISCLOSURE OF THE INVENTION

An object of the present invention is to provide a fluorous-tag-introduced fluoroamine which is ecological and advantageous for industrial use as a fluorinating agent because, after fluorination reaction with it, the load for separation and recovery of a product is low, to provide a method of producing the fluoroamine, to provide a fluorination method with the fluoroamine, and to provide a method of recovering a fluorous-tag-introduced amide.

The present inventors have assiduously studied so as to solve the above-mentioned problems, and have found that a fluoroamine with a specific fluorous-tag introduced thereinto may act as an excellent fluorinating agent for substrates having functional group containing oxygen, and after used in fluorination, it gives a fluorous-tag-introduced amide capable of being a starting material for the fluorinating agent and a fluorinated product that can be separated and recovered with ease, and therefore the fluoroamine can solve the above-mentioned problems; and based on these findings, the inventors have reached the present invention. Specifically, the present invention relates to the following (1) to (6):

(1) A fluoroamine of a general formula (I):

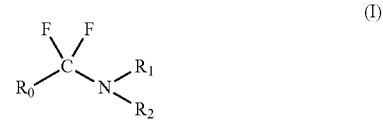

(In the formula, $R_0$ represents an alkyl group or an aryl group having from 1 to 3 substituents of Rf—$(CH_2)_m$—; Rf represents a perfluoroalkyl group having from 4 to 15 carbon atoms; m indicates from 0 to 2. $R_1$ and $R_2$ each represent a hydrogen atom, or an alkyl group or an aryl group optionally having a substituent; and these may be the same or different. At least two of $R_0$, $R_1$ and $R_2$ may be bonded to each other to form a ring.)

(2) The fluoroamine in the above (1), wherein in the general formula (I), $R_0$ is a phenyl group having from 1 to 3 substituents of Rf—$(CH_2)_m$—.

(3) A method for producing a fluoroamine in the above (1), which comprises fluorinating an amide of a general formula (II):

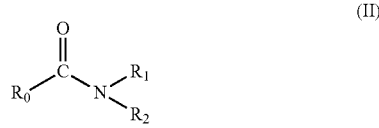

(In the Formula, $R_0$, $R_1$ and $R_2$ are the Same as Above.)

(4) A method for fluorination of a substrate having functional group containing oxygen, in which a fluoroamine in the above (1) is used.

(5) A recovery method comprising reacting a fluoroamine in the above (1) with a substrate having functional group containing oxygen to give an amide of the general formula (II) and a fluorinated product, and then adding both a fluorous solvent having at least 5 carbon atoms also having an atomic ratio of [fluorine/carbon] in the molecule of at least 1.5, and an organic solvent immiscible with the fluorous solvent at room temperature, to the reaction product to thereby extract and separate the amide in the fluorous solvent and recover it, and extract and separate the fluorinated product in the organic solvent and recover it.

(6) A recovery method comprising reacting a fluoroamine in the above (1) with a substrate having functional group containing oxygen to give an amide of the general formula (II) and a fluorinated product, and then adding an organic solvent having a dielectric constant of at most 5 to the reaction product to thereby precipitate and recover the amide, and extract and separate the fluorinated product in the organic solvent and recover it.

According to the present invention, there are provided a fluorous-tag-introduced fluoroamine which is ecological and advantageous for industrial use as a fluorinating agent because, after fluorination with it, the load for separation and recovery of the product is low, and a method of producing the fluoroamine, and a fluorination method with the fluoroamine, and a method of recovering a fluorous-tag-introduced amide.

BEST MODE FOR CARRYING OUT THE INVENTION

The fluoroamine of the present invention is represented by the following general formula (I), and is produced from a starting material of an amide represented by the following general formula (II):

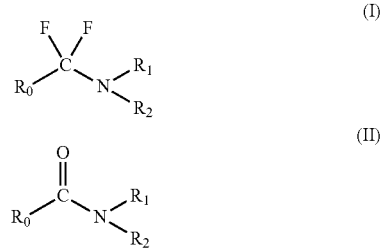

(In the formulae, $R_0$ represents an alkyl group or an aryl group having from 1 to 3 substituents of $Rf-(CH_2)_m-$; Rf represents a perfluoroalkyl group having from 4 to 15 carbon atoms; m indicates from 0 to 2. $R_1$ and $R_2$ each represent a hydrogen atom, or an alkyl group or an aryl group optionally having a substituent; and these may be the same or different. And at least two of $R_0$, $R_1$ and $R_2$ may be bonded to each other to form a ring.)

$R_0$ in the compounds of the general formulae (I) and (II) is an alkyl group or an aryl group having from 1 to 3 substituents of $Rf-(CH_2)_m-$. When the group has 2 or 3 such substituents, they may be the same or different.

Rf is a perfluoroalkyl group having from 4 to 15 carbon atoms, and is a substituent introduced into the compounds as a fluorous-tag. Rf may be linear, branched or cyclic, and the alkyl group constituting the perfluoroalkyl group includes butyl, isobutyl, t-butyl, pentyl, hexyl, heptyl, octyl, 2-ethylhexyl, nonyl, decyl, cyclohexyl, decalyl, etc. And, m is from 0 to 2.

The alkyl group for $R_0$ is preferably a linear or branched one having from 1 to 30 carbon atoms, including, for example, methyl, ethyl, propyl, isopropyl, butyl, isobutyl, t-butyl, pentyl, hexyl, heptyl, octyl, 2-ethylhexyl, nonyl, decyl, cyclohexyl, cyclohexyloxy, decalyl, norbornyl, bicyclohexyl, adamantyl, and their isomers, and, in addition, further including hydroxymethyl, hydroxyethyl, hydroxypropyl, hydroxybutyl, hydroxyphenyl, etc.

The aryl group for $R_0$ is preferably one having from 6 to 30 carbon atoms, including, for example, phenyl, o-tolyl, m-tolyl, p-tolyl, dimethylphenyl and its position isomers, cumyl, mesityl, trimethylphenyl and its isomers, hydroxyphenyl and its isomers, methoxyphenyl and its isomers, ethoxyphenyl and its isomers, alkyloxyphenyl and its isomers, naphthyl, methylnaphthyl, dimethylnaphthyl, hydroxynaphthyl, biphenyl, tetralyl, t-phenyl, anthryl, benzothienyl, chromenyl, indoyl, etc.

These alkyl group and aryl group may contain any other functional group, for example, a hydroxyl group, a halogen, a nitro group, a mercapto group, an amino group, an amide group, a cyano group, a carbonyl group, a carboxyl group, an acetyl group, an acyl group, an alkoxy group, and a sulfone group, other atomic groups and the like, and they may form isomers.

Of those, phenyl is preferred from the viewpoint of easiness in production.

$R_1$ and $R_2$ in the compounds of the general formulae (I) and (II) in the present invention each are a hydrogen atom, or an alkyl group or an aryl group optionally having a substituent; and they may be the same or different.

For the alkyl group and the aryl group for $R_1$ and $R_2$, referred to are the same as those exemplified hereinabove for $R_0$.

Of those, preferred are methyl, ethyl, propyl and isopropyl from the viewpoint of easiness in production.

At least any two of $R_0$, $R_1$ and $R_2$ may be bonded to each other to form a ring, and its examples include pyrrolidin-1-yl, morpholin-4-yl, piperidine-1-yl, etc.

The fluoroamine of the general formula (I) may be produced starting from the corresponding N,N-disubstituted amide compound of the general formula (II), and according to (i) a method of direct fluorine introduction thereinto using any of various fluorinating agents, or (ii) a method of fluorine introduction thereinto that comprises reaction with any other halogenating agent than a fluorinating agent followed by halogen exchange with a fluorine compound.

In the above method (ii), for example, when the agent for halogenation except fluorination is a chlorinating agent, then the oxygen atom of the amide bond is substituted with chlorine atoms by a chlorinating agent such as phosgene, phosphorus trichloride, phosphorus pentachloride, thionyl chloride, oxalyl chloride or the like.

In case where the chlorine reactivity is low, preferably, one having a high reactivity is selected from similar, bromine or iodine-containing halogenating agents for bromine or iodine introduction. For example, in a case of isobutyric amide, its chlorination may be completed by applying a phosgene flow thereto at 20° C. in dichloromethane (B. Haveaux, A. Dekoker, M. Rens, A. R. Sidani, J. Toye, and L. Ghosez, Organic Synthesis, CV 6, 282).

Next, the chlorinated product is processed according to an halogen exchange method using hydrogen fluoride, hydrogen fluoride/Lewis base, or alkali metal fluoride such as sodium fluoride, potassium fluoride or the like, thereby giving the intended fluoroamine of the general formula (I). The halogen exchange condition is difficult to define indiscriminately, which, however, may be determined with reference to known references, for example, G. A. Olah, J. T. Welch, Y. D. Vankar, M. Nojima, I. Kerekes, J. A. Olah, J. Org. Chem., 44, 3872 (1979); Yoshikazu Kimura, the Journal of Organic Synthetic Chemistry Society of Japan, 47, 258 (1989); and Y. Yoshida, Y. Kimura, J. Fluorine. Chem., 44, 291 (1989).

The starting material amide of the general formula (II) may be obtained by Heck reaction of the corresponding halogenated N,N-disubstituted amide compound and a perfluoro-substituted alkene with a Pd catalyst followed by hydrogenation reduction of the internal olefin with a Pd catalyst. The reaction condition is difficult to define indiscriminately, which, however, may be determined with reference to known references, for example, S. A. Buntin and R. F. Heck, Organic Synthesis, CV 7, 361; and Arthur C. Cope and Elbert C. Herrick, Organic Synthesis, CV 4, 304.

The fluoroamine of the general formula (I) obtained according to the above-mentioned production method may be favorably used, directly as it is, for fluorination of a substrate having functional group containing oxygen.

The substrate having functional group containing oxygen is an organic compound, a polymer and the like having the functional group, including, for example, primary, secondary or tertiary alcohols having a single hydroxyl group as the functional group; polyols, and saccharides such as glycosides, monose anhydrides, oligosaccharides and polysaccharides having at least 2 hydroxyl groups; compounds having a carbonyl group, such as aldehydes, ketones, carboxylic acids, etc.

The fluorination method of the substrate with the fluoroamine is not specifically defined, to which is applicable any ordinary technique heretofore employed in the art. In the fluorination, the fluoroamine is used preferably in an amount of from 0.8 to 2.2 equivalents relative to the substrate, and an inert solvent and diluent may be used. The fluorination may be effected under irradiation with microwaves having a frequency of from 1 to 30 GHz and/or electromagnetic waves near to microwaves, having a frequency of at most 1 GHz or from 30 to 300 GHz.

The fluoroamine may be subjected to distillation and has high thermal stability, and therefore, it may be used in fluorination or the like even within a temperature range of 150° C. or higher within which chemicals are heretofore difficult to handle.

One characteristic feature of the fluoroamine of the present invention is that a fluorous-tag is introduced into it. Owing to the fluorous property thereof, the amide of the general formula (II) and the fluorinated product to be produced through fluorination of the fluoroamine and the above-mentioned substrate may be readily separated and recovered. The recovered amide of the general formula (II) can be reused as the starting material in production of the above-mentioned fluoroamine.

Concretely, after the fluorination, a fluorous solvent and an organic solvent not miscible with the fluorous solvent at room temperature are added to the above-mentioned reaction product, preferably the condensed product obtained through condensation of the fluorination reaction liquid, thereby extracting and separating the amide of the general formula (II) in the fluorous solvent to recover it, and extracting and separating the fluorinated product in the organic solvent to recover it.

The fluorous solvent to be used herein is a fluorous solvent having at least 5 carbon atoms and having an atomic ratio of [fluorine/carbon] in the molecule of at least 1.5. Various commercial products are available as the fluorous solvent of the type. One or more of these may be used either singly or as combined.

The organic solvent not miscible with the fluorous solvent at room temperature could not be indiscriminately defined, as varying depending on the fluorous solvent. For example, for the fluorous solvent having a strong fluorous property such as perfluoroalkane, preferred are non-polar organic solvents such as hydrocarbons and chlorine-containing solvents. For the fluorous solvent having a weak fluorous property such as hydrofluoroether, preferred are hydrous polar solvents such as acetonitrile.

The amount of the solvents and the ratio of the fluorous solvent to the organic solvent separable from the fluorous solvent at room temperature in carrying out the above-mentioned separation treatment could not be indiscriminately defined, as being selected depending on the fluorinating agent used for the reaction, and on the type of the substrate and the type of the solvent. For example, the solvent amount may be within a range of from 5 to 200 times by mass the fluoroamine of the general formula (I) used in the reaction, and the ratio between the fluorous solvent and the organic solvent separable from the fluorous solvent may be within a range of from 0.2 to 4 in terms of the ratio by volume of the organic solvent to the fluorous solvent. Not specifically defined, the operation temperature may be one not higher than the boiling point of the solvent, and for example, it may be within a temperature range, or the system may be cooled to 0° C. or lower for the purpose of improving the selectivity in extraction and separation.

Apart from the method of using the above-mentioned fluorous solvent, also employable is a method of adding an organic solvent having a dielectric constant of at most 5 to the above reaction product after the termination of the fluorination reaction, preferably the concentrated product obtained by concentrating the fluorination reaction liquid, thereby precipitating and recovering the amide of the general formula (II) and extracting and separating the fluorinated product in the organic solvent to recover it.

The organic solvent having a dielectric constant of at most 5 is mainly a hydrocarbon-based organic solvent, for example, hexane, benzene, toluene, etc. (See "Solvent Handbook" by Kodansha, p. 883.)

Not specifically defined, the operation temperature may be one not higher than the boiling point of the solvent, and for example, it may be within a room temperature range, or the system may be cooled to 0° C. or lower for the purpose of improving the selectivity in separation.

EXAMPLES

The present invention is described in more detail with reference to the following Examples. The compounds in these Examples were analyzed with any of the following instruments.

Nuclear Magnetic Resonance Spectrometry (NMR)
$^1$H NMR (400 MHz): JEOL JNM-A400II
$^{13}$C NMR (100 MHz): JEOL JNM-A400II
$^{19}$F NMR (376 MHz): JEOL JNM-A400II (*1), or BRUKER MSL400 (*2)
IR Absorptiometry (IR)
JASCO FT/IR-410 (*1), or JASCO FT/IR-5300 (*2)
High-Resolution Mass Spectrometry (HRMS)
HRMS: JEOL JMS-FABmate, JEOL JMS-700TZ Example 1 a) Production of N,N-diethyl-4-(1H,2H-perfluoro-1-decenyl)benzamide (Compound a)

In a nitrogen atmosphere, 1.2 g (4 mmol) of N,N-diethyl-4-iodobenzamide, 2.0 g (4.4 mmol) of 1H,1H,2H-perfluorodecene, 9.0 mg (0.04 mmol) of palladium acetate, 0.26 g (0.8 mmol) of tetra-n-butylammonium bromide, 0.43 g (5.2 mmol) of sodium acetate, and 20 ml of anhydrous N,N-dimethylformamide (anhydrous DMF) were put into a 50-ml three-neck flask, and stirred at 125° C. for 24 hours. After cooled to room temperature, this was extracted with a solvent dichloromethane, and then the organic layer was washed twice with water. After concentrated, this was purified through silica gel column chromatography (solvent: dichloromethane/diethyl ether=5/1, by volume) to give a white solid of the compound a at a yield of 78%.

Spectral Data of Compound a
IR (KBr)*$^1$: 3041, 2985, 2939, 1616, 1474, 1120, 1147, 1102, 986 cm$^{-1}$
$^1$H NMR (CDCl$_3$): d=7.52 (d, J=8.11, 2H), d=7.42 (d, J=8.24, 2H), d=7.18 (dt, J=16.22, J=2.32, 1H), d=6.24 (dt, J=16.04, J=12.13, 1H), d=3.55 (s(b), 2H), d=3.25 (s(b), 2H), d=1.26 (s(b), 3H), d=1.12 (s(b), 3H)
$^{19}$F NMR (CDCl$_3$)*$^1$: d=−81.31 (t, J=10.0, 3F), d=−111.80 (dt, J=12.3, J=12.2, 2F), d=−121.92 (m, 2F), d=−122.46 (m, 4F), d=−123.26 (m, 2F), d=−123.67 (m, 2F), d=−126.65 (m, 2F)
$^{13}$C NMR (CDCl$_3$): d=170.31 (s, 1C), d=138.95 (s, 1C), d=138.92 (t, J=9.7, 1C), d=134.19 (s, 1C), d=127.70 (s, 2C), d=127.01 (s, 2C), d=115.37 (t, J=23.0, 1C), d=43.22 (s(b), 1C), d =39.37 (s(b), 1C), d=14.24 (s(b), 1C), d=12.88 (s(b), 1C)
HRMS (EI): Calculated for C$_{21}$H$_{16}$NOF$_{17}$(M$^+$): 621.0995, Found: m/z 621.0974 b) Production of N,N-diethyl-4-(1H,1H,2H,2H-perfluorodecyl)benzamide (Compound b)

0.16 g (0.25 mmol) of the compound a, 0.0333 g of 10% Pd/C, and 2 ml of ethyl acetate were put into a glass container. The reaction system was degassed under suction, and then purged with hydrogen gas followed by stirring at room temperature for 22 hours. The reaction mixture was filtered through Celite, and the filtrate was concentrated to give a white solid of the compound b at a yield of 96%.

Spectral Data of Compound b
IR(KBr)*$^2$: 3437, 2986, 1616, 1244, 1206, 1148, 1011, 866 cm$^{-1}$
$^1$H NMR (CDCl$_3$): d=7.34 (d, J=8.11, 2H), d=7.24 (d, J=8.06, 2H), d=3.54 (s(b), 2H), d=3.26 (s(b), 2H), d=2.92-2.96 (m, 2H), d=2.31-2.44 (m, 2H), d=1.24 (s(b), 3H), d=1.12 (s(b), 3H)
$^{19}$F NMR (CDCl$_3$)*$^1$: d=−81.31 (t, J=9.7, 3F), d=−115.13 (tt, J=17.7, J=14.0, 2F), d=−122.23 (m, 2F), d=−122.46 (m, 4F), d=−123.25 (m, 2F), d=−124.00 (m, 2F), d=−126.65 (m, 2F)
$^{13}$C NMR (CDCl$_3$): d=170.96 (s, 1C), d=140.13 (s, 1C), d=135.85 (s, 1C), d=128.27 (s, 2C), d=126.83 (s, 2C), d=43.23 (s(b), 1C), d=39.25 (s(b), 1C), d=32.74 (t, J=22.3, 1C), d=26.25 (t, J=4.4, 1C), d=14.13 (s(b), 1C), d=12.84 (s(b), 1C)
HRMS (EI): Calculated for C$_{21}$H$_{18}$NOF$_{17}$(M$^+$): 623.1116, Found: m/z 623.1122 c) Production of N,N-diethyl-α,α-difluoro[4-(1H,1H,2H,2H-perfluorodecyl)benzyl]amine (Compound c)

In a nitrogen atmosphere, 18.7 g (30 mmol) of the compound b, and 50 ml of dichloromethane were put into a glass container, and with stirring, 4.2 g (33 mmol) of oxalyl chloride was dropwise added thereto. After the addition, this was heated under reflux and stirred for 24 hours. This was cooled to 0° C., then 3.7 g (23 mmol) of triethylamine-trihydrofluoride was dropwise added thereto, and thereafter 4.65 g (46 mmol) of triethylamine was dropwise added thereto. After the addition, this was restored to room temperature, and in a nitrogen atmosphere, the solid was collected by filtration and the residue was washed with hexane. The filtrate was concentrated, again followed by filtration and washing with hexane in a nitrogen atmosphere. The filtrate was concentrated and subjected to reduced pressure distillation (150° C.) using a vacuum pump, thereby giving a white solid of the compound c at a yield of 87%.

Spectral Data of Compound c
$^1$H NMR (CDCl$_3$): d=7.56 (d, J=8.12, 2H), d=7.27 (d, J=7.76, 2H), d=2.94-2.98 (m, 2H), d=2.89 (q, J=7.08, 4H), d=2.33-2.46 (m, 2H), d=1.06 (t, J=6.96, 6H)
$^{19}$F NMR (CDCl$_3$)*$^2$: d=−73.79 (s, 2F), d=−81.85 (s, 3F), d=−116.63 (s, 2F), d=−123.40 (s, 2F), d=−123.63 (s, 4F), d=−124.41 (s, 2F), d=−125.07 (s, 2F) d=−127.82 (s, 2F)
*2: Measured at −50° C.

Example 2 d) Production of N,N-diethyl-3,5-bis(1H,2H-perfluoro-1-decenyl)benzamide (Compound d)

In a nitrogen atmosphere, 0.2 g (0.5 mmol) of N,N-diethyl-3,5-diiodobenzamide, 0.5 g (1.1 mmol) of 1H,1H,2H-perfluorodecene, 5.6 mg (0.025 mmol) of palladium acetate, 65 mg (0.2 mmol) of tetra-n-butylammonium bromide, 0.11 g (1.3 mmol) of sodium acetate, and 5 ml of anhydrous DMF were put into a 25-ml three-neck flask, and stirred at 115° C. for 4 days. After cooled to room temperature, this was extracted with a solvent dichloromethane, and then the organic layer was washed twice with water. After concentrated, this was purified through silica gel column chromatography (solvent: dichloromethane/diethyl ether=10/1, by volume) to give a white solid of the compound d at a yield of 56%.

Spectral Data of Compound d
IR (KBr)*$^1$: 2992, 1617, 1480, 1371, 1241, 1214, 1149, 979, 657 cm$^{-1}$
$^1$H NMR (CDCl$_3$): d=7.57 (s, 1H), d=7.51 (s, 2H), d=7.20 (d, J=16.16, 2H), d=6.29 (dt, J=16.04, J=11.83, 2H), d=3.57 (s(b), 2H), d=3.28 (s(b), 2H), d=1.28 (s(b), 3H) d=1.15 (s(b), 3H)
$^{19}$F NMR (CDCl$_3$)*$^1$: d=−81.31 (t, J=9.7, 6F), d=−112.01 (dt, J=12.2, J=12.2, 4F), d=−121.87 (m, 4F), d=−122.43 (m, 8F), d=−123.24 (m, 4F), d=−123.61 (m, 4F), d=−126.64 (m, 4F)

¹³C NMR (CDCl₃): d=169.44 (s, 1C), d=139.10 (s, 2C), d=138.15 (t, J=9.1, 2C), d=134.75 (s, 1C), d=127.48 (s, 1C), d=126.58 (s, 2C), d=116.75 (t, J=23.1, 2C), d=43.41 (s(b), 1C), d=39.50 (s(b), 1C), d=14.25 (s(b), 1C), d=12.87 (s(b), 1C)

HRMS (ESI): Calculated for $C_{31}H_{17}NOF_{34}Na$ ((M+Na)⁺): 1088.0675,
Found: m/z 1088.0670 e) Production of N,N-diethyl-3,5-bis(1H,1H,2H,2H-perfluorodecyl)benzamide (Compound e)

1.2 g (1.12 mmol) of the compound d, 0.1983 g of a catalyst 10% Pd/C, and 45 ml of ethyl acetate were put into a glass container. The reaction system was degassed under suction, and then purged with hydrogen gas followed by stirring at room temperature for 22 hours. The reaction mixture was filtered through Celite, and the filtrate was concentrated to give a white solid of the compound e at a yield of 99%.
Spectral Data of Compound e
IR(KBr)*¹: 2988, 1638, 1437, 1371, 1142, 872, 822, 664 cm⁻¹
¹H NMR (CDCl₃): d=7.10 (s, 3H), d=3.55 (s(b), 2H), d=3.23 (s(b), 2H), d=2.91-2.95 (m, 4H), d=2.31-2.45 (m, 4H), d=1.26 (s(b), 3H), d=1.11 (s(b), 3H)
¹⁹F NMR (CDCl₃)*¹: d=−81.31 (t, J=10.4, 6F), d=−115.02 (tt, J=16.5, J=14.6, 4F), d=−122.20 (m, 4F), d=−122.43 (m, 8F), d=−123.24 (m, 4F), d=−123.96 (m, 4F), d=−126.64 (m, 4F)
¹³C NMR (CDCl₃): d=170.74 (s, 1C), d=140.15 (s, 2C), d=138.57 (s, 1C), d=129.06 (s, 1C), d=124.54 (s, 2C), d=43.26 (s(b), 1C), d=39.29 (s(b), 1C), d=32.72 (t, J=22.2, 2C), d=26.33 (t, J=4.2, 2C), d=14.08 (s(b), 1C), d=12.79 (s(b), 1C)
HRMS (ESI): Calculated for $C_{31}H_{21}NOF_{34}Na$ ((M+Na)⁺): 1092.0989,
Found: m/z 1092.0984 f) Production of N,N-diethyl-α,α-difluoro[3,5-bis(1H,1H,2H,2H-perfluorodecyl)benzyl]amine (Compound f)

In a nitrogen atmosphere, 15.9 g (14.9 mmol) of the compound e, and 30 ml of dichloromethane were put into a glass container, and with stirring, 2.08 g (16.4 mmol) of oxalyl chloride was dropwise added thereto. After the addition, this was heated under reflux and stirred for 24 hours. This was cooled to room temperature, then 1.85 g (11.5 mmol) of triethylamine-trihydrofluoride was dropwise added thereto, then cooled to 0° C., and thereafter 2.32 g (23 mmol) of triethylamine was dropwise added thereto. After the addition, this was restored to room temperature, and in a nitrogen atmosphere, the solid was collected by filtration and the residue was washed with hexane. The filtrate was concentrated, again followed by filtration and washing with hexane in a nitrogen atmosphere. The filtrate was concentrated and subjected to reduced pressure distillation (200° C.) using a vacuum pump, thereby giving a white solid of the compound f at a yield of 84%.
Spectral Data of Compound f
¹H NMR (CDCl₃): d=7.34 (d, J=0.97, 2H), d=7.14 (s, 1H), d=2.93-2.97 (m, 4H), d=2.87 (q, J=7.08, 4H), d=2.32-2.45 (m, 4H), d=1.06 (t, J=7.08, 6H)
¹⁹F NMR (CDCl₃)*²: d=−73.92 (s, 2F), d=−81.31 (s, 6F), d=−114.93 (s, 4F), d=−122.01 (s, 4F), d=−122.34 (s, 8F), d=−123.15 (s, 4F), d=−123.81 (s, 4F), d=−128.59 (s, 4F)

Example 3

Fluorination of Dodecanol 93 mg (0.5 mmol) of dodecanol purified by distillation, 0.39 g (0.6 mmol, 1.2 equivalents) of N,N-diethyl-α,α-difluoro-[4-(1H,1H,2H,2H-perfluorodecyl)benzyl]amine (compound c) produced in Example 1, and 0.5 ml of heptane were put into a container formed of PFA (tetrafluoroethylene/perfluoroalkyl vinyl ether copolymer), and reacted in a nitrogen atmosphere at 100° C. for 3 hours. After the reaction, an aqueous saturated sodium hydrogencarbonate solution was added thereto for neutralization, and then the product was extracted out with dichloromethane. The solvent was evaporated away, followed by purification through silica gel column chromatography (solvent: dichloromethane/diethyl ether mixed solvent) to give a product. The main product was 1-fluorododecane, and its yield was 86%.
Spectral Data of the Product (1-fluorododecane)
IR(neat)*²: 2926, 2855, 1468, 1007 cm⁻¹
¹H NMR (CDCl₃): d=4.44 (dt, J=47.27, J=6.22, 2H), d=1.59-1.78 (m, 2H), d=1.26-1.42 (m, 18H), d=0.88 (t, J=6.34, 3H)
¹³C NMR (CDCl₃): d=84.23 (d, J=163.8, 1C), d=31.92 (s, 1C), d=30.42 (d, J=19.8, 1C), d=29.64 (s, 1C), d=29.63 (s, 1C), d=29.56 (s, 1C), d=29.52 (s, 1C), d=29.35 (s, 1C), d=29.25 (s, 1C), d=25.15 (d, J=5.8, 1C), d=22.68 (s, 1C), d=14.10 (s, 1C)
¹⁹F NMR (CDCl₃)*¹: d=−218.53 (dt, J=47.0, J=25.0, 1F)

Example 4

Fluorination of Dodecanol

This is the same as in Example 3, except that the fluorinating agent was changed to N,N-diethyl-α,α-difluoro-[3,5-bis(1H,1H,2H,2H-perfluorodecyl)benzyl]amine (compound f) produced in Example 2. The main product was 1-fluorododecane, and its yield was 88%.

Example 5

Fluorination of Butyl 5-Hydroxypentanoate 87 mg (0.5 mmol) of butyl 5-hydroxypropionate purified by distillation, 0.39 g (0.6 mmol, 1.2 equivalents) of N,N-diethyl-α,α-difluoro-[4-(1H,1H,2H,2H-perfluorodecyl)benzyl]amine (compound c) produced in Example 1, and 0.5 ml of heptane were put into a PFA container, and reacted in a nitrogen atmosphere at 100° C. for 3 hours. After the reaction, an aqueous saturated sodium hydrogencarbonate solution was added thereto for neutralization, and then the product was extracted out with dichloromethane. The solvent was evaporated away, followed by purification through silica gel column chromatography (solvent: dichloromethane/diethyl ether mixed solvent) to give a product. The main product was butyl 5-fluoropentanoate, and its yield was 92%.
Spectral Data of the Product (butyl 5-fluoropentanoate)
IR(neat)*²: 2963, 1736, 1460, 1173, 1042 cm⁻¹
¹H NMR (CDCl₃): d=4.46 (dt, J=47.22, J=5.76, 2H), d=4.08 (t, J=6.62, 2H), d=2.36 (t, J=7.04, 2H), d=1.56-1.84 (m, 6H), d=1.31-1.45 (m, 2H), d=0.94 (t, J=7.28, 3H)
¹³C NMR (CDCl₃): d=173.34 (s, 1C), d=83.58 (d, J=164.6, 1C), d=64.24 (s, 1C), d=33.72 (s, 1C), d=30.65 (s, 1C), d 29.75 (d, J=19.8, 1C), d=20.83 (d, J=5.0, 1C), d=19.10 (s, 1C), d=13.66 (s, 1C)
¹⁹F NMR (CDCl₃)*¹: d=−219.45 (dt, J=47.6, J=25.1, 1F)

Example 6

Fluorination of Butyl 5-Hydroxypentanoate

This is the same as in Example 5, except that the fluorinating agent was changed to N,N-diethyl-α,α-difluoro-[3,5-bis(1H,1H,2H,2H-perfluorodecyl)benzyl]amine (compound f) produced in Example 2. The main product was butyl 5-fluoropentanoate, and its yield was 87%.

Example 7

After the same reaction as in Example 3, the reaction liquid was concentrated to remove the solvent. 5 ml of hexane (dielectric constant: 1.89) was added to the residue, and cooled to −30° C. with fully stirring, and then the precipitated product was collected by filtration, and washed with cold hexane at −30° C. The obtained solid residue and the filtrate were separately analyzed, and as a result, N,N-diethyl-4-(1H,1H,2H,2H-perfluorodecyl)benzamide (compound b) having a purity of 99% was separated and recovered from the solid at a yield of 93%. From the filtrate, 1-fluorododecane having a purity of 92% was separated, and its yield was 87%.

Example 8

After the same reaction as in Example 4, the reaction liquid was concentrated to remove the solvent. 20 ml of a fluorous solvent, PFMC (perfluoromethylcyclohexane, having 7 carbon atoms and having an atomic ratio [fluorine/carbon] of 2) and 10 ml of toluene (dielectric constant: 2.24) were added to the residue, and well stirred. The two layers separated when kept statically at room temperature were individually collected. The same operation was repeated twice, and the individual layers were analyzed. As a result, N,N-diethyl-3,5-bis(1H,1H,2H,2H-perfluorodecyl)benzamide (compound e) having a purity of 92% was partitioned in the fluorous solvent layer at a yield of 97%; and 1-fluorododecane having a purity of 99% was in the organic layer at a yield of 75%.

Example 9

After the same reaction as in Example 6, the reaction liquid was concentrated to remove the solvent. 10 ml of a mixed solvent (1/1 by volume) of fluorous solvents, FC-77 (3M company's trade name, having 8 carbon atoms and having an atomic ratio [fluorine/carbon] of from 2 to 2.25 (mixture of $C_8F_{18}$ and $C_8F_{16}O$)) and HFE-7100 (3M company's trade name, having 5 carbon atoms and having an atomic ratio [fluorine/carbon] of 1.8), and 10 ml of 5 mass % hydrous acetonitrile were added to the residue, and well stirred. The two layers separated when kept statically at room temperature were individually collected and analyzed. As a result, N,N-diethyl-3,5-bis(1H,1H,2H,2H-perfluorodecyl)benzamide (compound e) having a purity of 98% was partitioned in the fluorous solvent layer at a yield of 94%; and butyl 5-fluoropentanoate having a purity of 99% was in the organic layer at a yield of 72%.

INDUSTRIAL APPLICABILITY

The fluoroamine of the present invention may be subjected to distillation and has high thermal stability, and therefore, it may be used in fluorination within a temperature range of 150° C. or higher within which chemicals were heretofore difficult to handle, thereby producing fluorine compounds especially useful in the field of medicines and agricultural chemicals.

Further, since a fluorous-tag is introduced thereinto, the fluoroamine realizes an ecological industrial process in which, after fluorination with it, an amide recyclable as a starting materials for production of the fluoroamine can be readily separated and recovered.

The invention claimed is:

1. A fluoroamine of a general formula (I):

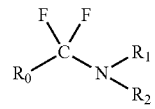

(I)

(wherein $R_0$ is a phenyl-group having from 1 to 3 substituents of Rf—$(CH_2)_m$—; Rf represents a perfluoroalkyl group having from 4 to 15 carbon atoms; m indicates from 1 to 2; $R_1$ and $R_2$ each represent a hydrogen atom, or an alkyl group or an aryl group optionally having a substituent, and these may be the same or different; at least two of $R_0$, $R_1$ and $R_2$ may be bonded to each other to form a ring).

2. A method for producing a fluoroamine of claim 1, which comprises fluorinating an amide of a general formula (II):

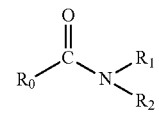

(II)

(wherein $R_0$, $R_1$ and $R_2$ are the same as above).

3. A method for fluorination of a substrate having functional group containing oxygen, in which a fluoroamine of claim 1 is used.

4. A recovery method comprising reacting a fluoroamine of claim 1 with a substrate having functional group containing oxygen to give an amide of a general formula (II) and a fluorinated product, and then adding both a fluorous solvent having at least 5 carbon atoms also having an atomic ratio of [fluorine/carbon] in the molecule of at least 1.5, and an organic solvent immiscible with the fluorous solvent at room temperature, in a volume ratio [fluorous solvent/organic solvent] within a range of from 0.2 to 4, to the reaction product to thereby extract and separate the amide in the fluorous solvent and recover it, and extract and separate the fluorinated product in the organic solvent and recover it:

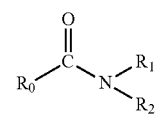

(II)

(wherein $R_0$, $R_1$ and $R_2$ are the same as above).

5. A recovery method comprising reacting a fluoroamine of claim 1 with a substrate having functional group containing oxygen to give an amide of a general formula (II) and a fluorinated product, and then adding an organic solvent having a dielectric constant of at most 5 to the reaction product to thereby precipitate and recover the amide, and extract and separate the fluorinated product in the organic solvent and recover it:

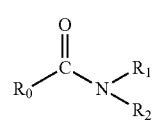
(II)
(wherein $R_0$, $R_1$ and $R_2$ are the same as above).
6. The fluoroamine as claimed in claim 1, wherein Rf is introduced as a fluorous-tag.
* * * * *